US007024006B1

(12) United States Patent
Schwartz et al.

(10) Patent No.: US 7,024,006 B1
(45) Date of Patent: Apr. 4, 2006

(54) COMPLEMENTARY-PAIR EQUALIZER

(75) Inventors: Stephen R. Schwartz, 172 Congdon St., Providence, RI (US) 02906; John H. Osmand, Providence, RI (US); Damian Kulash, Chicago, IL (US)

(73) Assignee: Stephen R. Schwartz, Providence, RI (US)

( * ) Notice: Subject to any disclaimer, the term of this patent is extended or adjusted under 35 U.S.C. 154(b) by 0 days.

(21) Appl. No.: 09/344,299

(22) Filed: Jun. 24, 1999

(51) Int. Cl.
*A61F 11/06* (2006.01)

(52) U.S. Cl. ....................... 381/98; 381/71.1; 381/94.7

(58) Field of Classification Search ............... 381/94.1, 381/94.2, 94.7, 943, 71.13, 98, 99, 100, 71.8, 381/71.1, 103, 92, 71.14, 941, 101, 102, 381/1, 17
See application file for complete search history.

(56) References Cited

U.S. PATENT DOCUMENTS 4,201,107 A * 5/1980 Barber, Jr. et al. ........... 84/743
4,409,435 A * 10/1983 Ono ........................... 381/317
4,524,667 A * 6/1985 Duncan ....................... 84/728
4,630,305 A * 12/1986 Borth et al. ............... 381/94.3
4,736,426 A * 4/1988 Kinoshita et al. .............. 381/1
4,748,669 A * 5/1988 Klayman ....................... 381/1
4,932,063 A * 6/1990 Nakamura ................. 381/94.1
4,947,440 A * 8/1990 Bateman et al. ............ 381/107
5,060,272 A * 10/1991 Suzuki ....................... 381/119
5,177,801 A * 1/1993 Shoda et al. ................ 381/119
5,291,558 A * 3/1994 Ross .......................... 381/107
5,301,236 A * 4/1994 Iizuka et al. .................. 381/17
5,414,776 A * 5/1995 Sims, Jr. ..................... 381/119
5,638,454 A * 6/1997 Jones et al.
5,809,843 A * 9/1998 Barger et al. ................. 74/574
5,939,656 A * 8/1999 Suda ........................... 84/630
6,246,773 B1 * 6/2001 Eastty ..................... 381/71.11
6,301,365 B1 * 10/2001 Yamada et al. ............. 381/119

* cited by examiner

*Primary Examiner*—Brian T. Pendleton
(74) *Attorney, Agent, or Firm*—Kenyon & Kenyon

(57) ABSTRACT

A method and apparatus are described which reduce the presence of an unwanted signal. According to one embodiment, a first signal is provided from a desired location that includes an unwanted signal while a second signal is provided from an alternate location (e.g., one where the unwanted signal is less of a proportion of the total signal). The first and alternate signals are provided to respective signal processors. A level for a selected frequency band of the first and alternate signals is adjusted so that an increase in one results in a decrease in the other. Doing so allows the frequncy band that includes the unwanted signal to be reduced in the desired first signal and filled in with a similar frequency band from the alternate signal.

25 Claims, 8 Drawing Sheets

COMPLEMENTARY-PAIR EQUALIZER

BACKGROUND OF THE INVENTION

The present invention deals with the field of signal modification. In particular, it deals with a method and device/s for the selection of frequency portions of at least two versions of a signal which are summed to create a signal which may be superior to, and/or avoid problems found in, one or more of the source signals.

When transducing audio signals to electrical signals, it is common to eliminate undesireable elements by the process of somehow filtering or equalizing those signals. For example, where a musical performance is recorded in a concert hall, problem noises are often caused by the noises made by lights, HVAC systems and blowers, etc. Some of these sounds may be more pronounced at some places than at others. It is common for there to be certain places where the overall sound is most desireable, even though such places may have specific problems, such as a particular buzz caused by a nearby light fixture. When a placement still seems optimum despite a problem, the common solution is to use a filter/equalizer to reduce the frequency band of the offending sound. The filter reduces all signal in the given frequency band, both the offending sound and the desired portions of the signal. In the circumstance where there is no desired signal in the given frequency band, this is not a problem. An example is when there is an undesireable high-pitched hiss as commonly given off by a steam radiator, and a person at a podium talking into a microphone. There is a good chance that there is little energy from the person that is in the frequency range of the hiss, so reducing that range drastically to reduce the offending hiss will not degrade the intelligiblity of the person.

However, if the steam radiator is sharing the room with a group of musical instruments, such as a chamber orchestra, certain elements of the music will be affected. Higher notes or instruments (such as flutes) may be affected more than others, thus changing the balance of notes and instruments from what the composer intended and the performers practiced. A sound engineer will seek to affect the musical sound as little as possible while eliminating the offending sound as much as possible. The typical result is a compromise where there is more of the offensive sound than desired, the music does not sound as good as it could, or both.

SUMMARY OF THE INVENTION

The solutions presented below may be tangentially related to certain aspects of a speaker crossover network, a common device in the audio field. Loudspeaker systems are made of separate speaker elements, such as woofers (low frequency drivers), tweeters (high frequency drivers), and midrange drivers. Each element is optimized for a specific and limited frequency band, and requires the absence of frequencies not in its limited frequency band. A common speaker crossover divides an incoming signal into 2 or more frequency bands for distribution to separate speaker elements.

According to an embodiment of the present invention, filters/equalizers/etc. are constructed to include a second signal path, whose frequency response is essentially the inverse of the original signal path. This second signal path is coupled with a second source of the signal, which is chosen only for its quality in the frequency band/s reduced in the first signal path. The first filtered signal and second 'inverse-filtered' signal are then summed, which may result in a signal similar in accuracy to the first signal path alone, and may also have an increase in the rejection of the undesired signal. In general, the two source signals are assumed to be of similar intensity within the pertinent frequency band/s, though compensation can likely be made when they are not.

In the example of the steam radiator and chamber orchestra above, a second signal may be supplied by a second microphone placed far from the offending steam sound. This may be in an odd corner of the room, which may not be good for the overall sound of the music—this second spot needs only to have an increase in ratio of desired sound (music) to undesired sound (steam hiss) in the frequency range of the undesired sound, as compared to the first signal in the same frequency range. As the apparatus is adjusted to decrease the energy of the original signal's offending frequency band, where the amount of unwanted noise is high, it simultaneously increases the energy in the same band of the second signal, where the amount of unwanted noise is low. The summing of the signals will provide an increase in the reduction of the unwanted noise, while maintaining the fidelity of the original music.

DETAILED DESCRIPTION

Figure 1:
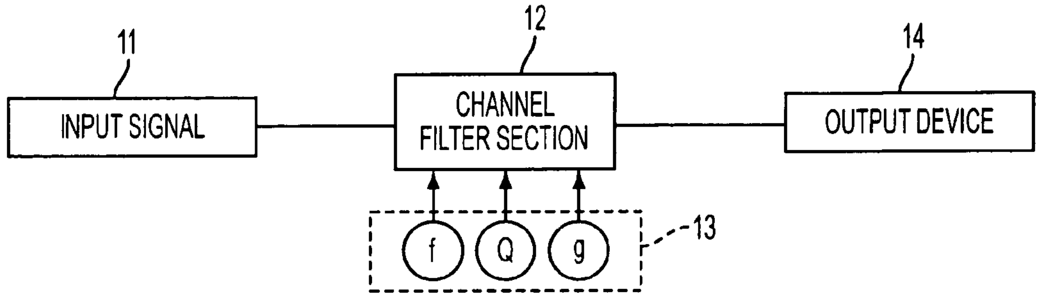
FIG. 1 PRIOR ART
FIG. 1 is a general block diagram of a typical prior art audio equalizer.

FIG. 1 is a general block diagram of a typical audio equalizer as is known in the art. The type shown here is for a single channel of a fully-parametric equalizer. An input signal 11 is fed to a filter circuit 12 whose parameters are determined by the controls 'f', 'Q' and 'g' 13. Control 'f' determines the center frequency of the affected area. Control 'Q' determines the bandwidth of the affected area. Control 'g' reduces (by convention, counterclockwise from center position) or increases (clockwise from center position) the signal in the area determined by the settings of 'f' and 'Q'. At the center setting of 'g', where there is no increase or decrease of signal, the settings of 'f' and 'Q' have no effect. The final signal may be sent to an output device 14. For some discussion below, it is helpful to refer to input signal 11 and filter circuit 12 as the PRIMARY input signal and filter circuit.

There are two basic categories of filters. The first category is that of the simple filter shapes known as highpass, lowpass, bandpass, and notch(i.e., band reject). When these are added to the original signal, an eq (equalizer) type filter is created.

Figure 2A:
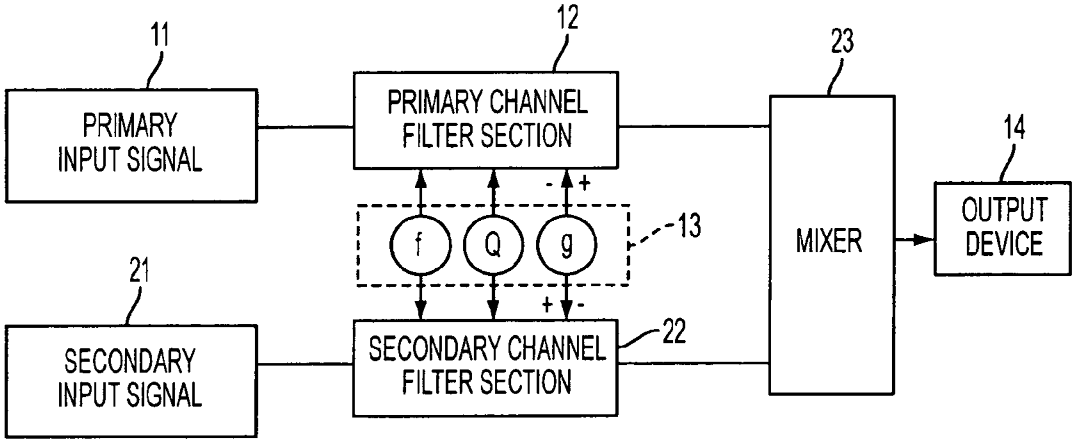
FIG. 2A is a general block diagram of an audio equalizer arranged for the addition of inverse filter elements, according to an embodiment of the present invention.

FIG. 2A is a general block diagram of an audio equalizer arranged for the addition of a complementary pair of inverse filter elements, according to an embodiment of the present invention. In this example, both filter elements 12 and 22 may be of the eq type. A second input signal 21 is fed to a second filter circuit 22, which may be identical to filter circuit 12. We refer to input signal 21 and filter circuit 22 as the SECONDARY or alternate input signal and filter circuit. Both filter circuits, 12 and 22, are controlled by the same single set of controls 13. However, the 'g' control's effect on the secondary circuit 22 may be the opposite of its effect on the primary circuit 12. Thus, as a particular frequency region is reduced by primary circuit 12, it is also increased by secondary circuit 22 by the same magnitude. The outputs are mixed by circuit 23, which may provide control (not shown) of the relative strength of outputs 12 and 22, if desired. Due to the nature of some signals, phase inversion switches may be desireable at suitable locations for any embodiment of the present invention.

The boost gain should complement the cut gain in a proportion that maintains the overall gain relationship on the outputs of 12 and 22 when combined. With no cut or boost, the band gain is 0 dB for both channels 12 and 22, and the sum of their outputs yields a gain of +6 dB, assuming similar in-phase signals. Thus, if channel 12's frequency band is reduced to minus infinity dB, channel 22's frequency band is boosted to +6 dB to compensate for the reduction. Conversely, if channel 12 is boosted +6 dB, channel 22 is reduced to minus infinity dB.

Another embodiment, similar to the device described above, configures primary channel 12 as eq with reduction filtering only, and configures secondary channel 22 as pass-band filtering with no flat setting. With gain control 'g' set to full gain (full clockwise) at primary channel 12, response is flat 0 dB gain for filter 12 and minus infinity dB for the entire bandwidth of filter 22. The output of mixer 23 is therefore the unaltered primary channel input 11 from channel 12, rather than the sum of channels 12 and 22 as above. As the selected frequencies of 12 are decreased, the corresponding frequencies of 22 are increased to "fill the holes" made by the activity of 12. When the selected frequencies of 12 are reduced to minus infinity dB, the corresponding frequencies of 22 are at unity gain. Filter channels 12 and 22 may have an input gain trim to adjust levels to compensate for differences in the input signals 11 and 21. The channel filters may have a switch to toggle function between these two arrangements.

If the primary and secondary inputs 11 and 21 were properly chosen, the result of the embodiment will be as described. For the example of the chamber orchestra and steam radiator above, the primary input signal 11 is from the microphone in the optimum spot for the sound of the orchestra, and the secondary input signal 21 is from the microphone in an odd corner of the room that is far from the steam radiator. The operator adjusts the controls for the best compromise between the good orchestra sound and least steam noise, as follows. The following process is facilitated by having separate volume controls at mixer 23. Step 2 involves first INCREASING the level of the offending sound because it is easier for a human operator to isolate a problem area by hearing it at a loud level, then reducing it as indicated in Step 3.

1—Turn off/down the secondary signal output, and set the controls for high gain ('g' clockwise from center) and 'Q' to about an octave.

2—Move frequency control 'f' so that the offending noise is at its loudest.

3—Set the gain control 'g' for strong cut (counter-clockwise from center).

4—Adjust the 'Q' control to be as narrow as possible, without significantly increasing the noise.

5—Fine tune frequency control 'f' for best rejection.

6—Repeat 4 and 5 as needed until an optimum is reached for frequency center and narrowest width, also adjusting gain control 'g' for as little cut as is optimum.

7—Add the secondary channel input to normal gain.

8—Adjust controls for optimum results. Repeat previous steps as needed.

Figure 9:
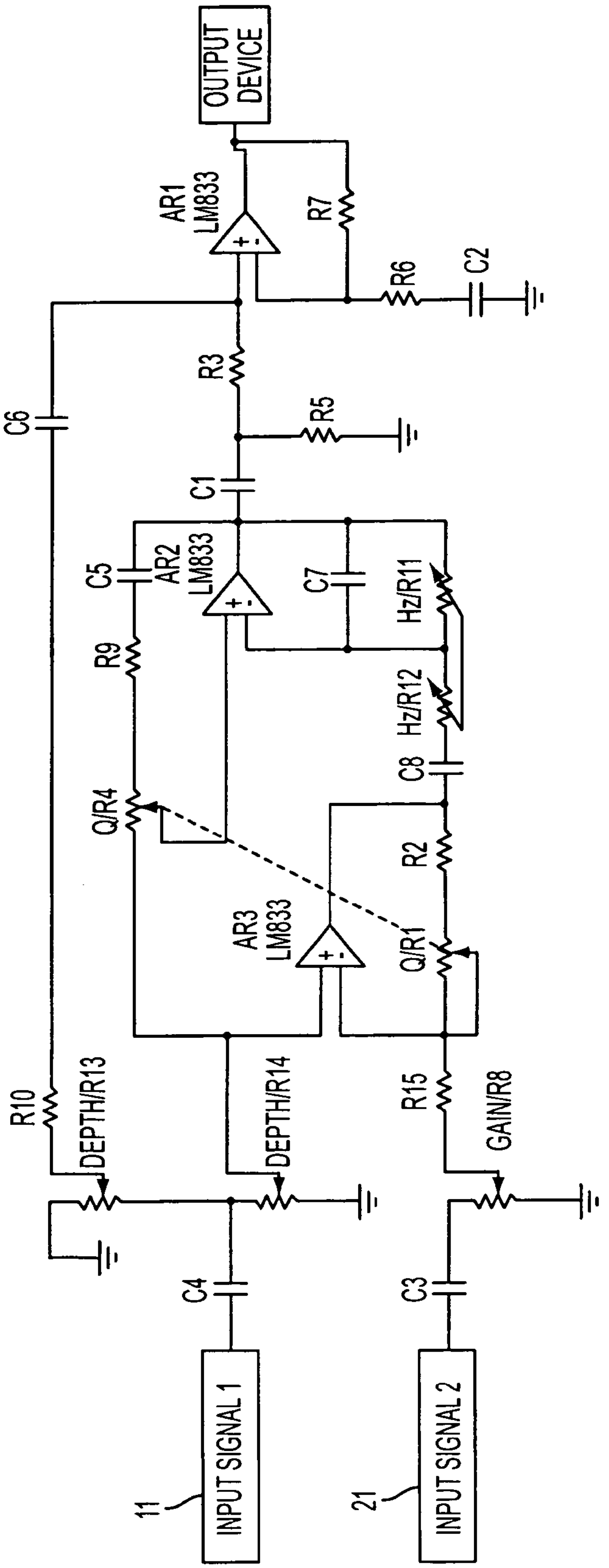
FIG. 9 is a schematic diagram of an embodiment of the present invention designed to perform simultaneous band-pass and band-reject of a pair of signals

FIG. 9 shows a schematic diagram of an implementation of a single band complementary pair equalizer which makes special use of signal phase relationships to accomplish both the primary signal band-reject (notch) filter and the secondary signal bandpass filter to be accomplished by a single circuit. Amplifier AR3 inverts secondary signal 21 and mixes it with in-phase primary signal 11. This mixed signal is fed through a bandpass filter (C7,C8,R11,R12, etc.) which is inverted by the inverting input of amplifier AR2. The resultant signal at this point is the selected passband region of the inverted phase primary signal 11 and the in-phase secondary signal 21. To this mixed signal is added the original in-phase primary signal, via R4. The portion of the mixed bandpass signal, which is the inverted phase region of the primary signal, cancels with the complementary portion of the in-phase complete primary signal and results in a band-reject (notch) filter for the primary signal. The portion of the mixed bandpass filter output signal that is the in-phase region of the secondary signal remains unaffected. Thus, the single bandpass circuit (C7,C8,R11,R12, etc.) suffices to perform a band-reject function on primary signal 11 and a bandpass function on secondary signal 21.

This implementation is only one of many possible ways to accomplish the task. Another possibility is to simply combine the primary and secondary signals, pass the combined signal through the bandpass filter, and add to the filter's output the primary signal unfiltered, but 180 degrees out of phase. It is important to get the phase relationships correct, making sure that the primary bandpassed signal is added to the original primary signal, these two bearing a 180 degree phase relationship to each other.

Figure 2B:
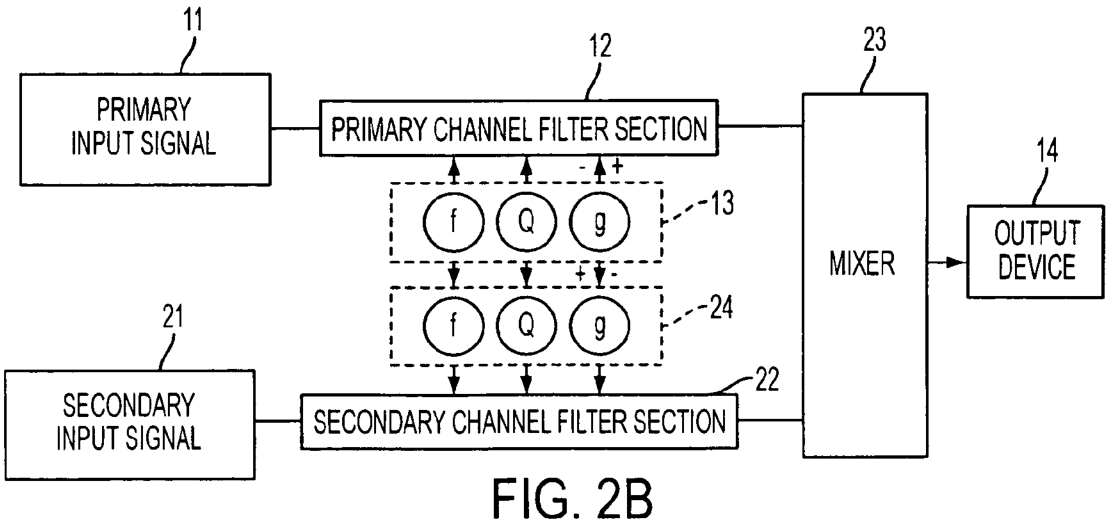
FIG. 2B is FIG. 2A, with an additional set of controls added to the secondary channel.

FIG. 2B is identical to FIG. 2A, except for the addition of a 2nd set of controls 24 which affect only Secondary Channel EQ 22. Because of the complexity of some signals, the imperfection of any physical embodiments, etc., it may be advantageous to provide this set to allow the parameters of the secondary path's filters to be varied from the positions set by the primary controls 13 (widen or narrow the Q, sweep the frequency up/down, increase/reduce the gain). Operation is as described as for FIG. 2A, but would add a step at the end for fine tuning with the controls 24.

The device may be constructed with multiple bands (sections), each section operating in the same way. Prior art audio equalizers currently used for the purposes of the example above generally contain 3, 4 or 5 bands. Care must be given to the arrangement of the filter elements (re: parallel, series, etc.) so that each complementary primary/secondary pair achieves the desired result. This phenomenum is known in the art, and is dependent on the type of filter element used.

Mentioned above are two basic categories of filters. The first category is that of the simple filter shapes known as highpass, lowpass, bandpass, and notch (i.e., band reject). These may be mathematically represented by T(s), where s is the complex frequency and T(s) is the voltage transfer function of the complex frequency. When these are added to the original signal, an eq (equalizer) type filter is created. An equalizer can be crudely represented by (1−T(s)), and its complement would be (1+T(s)). For audio purposes in general, a group of simple filters usually works best arranged in parallel (where transfer functions are added), and a group of eq type filters works best arranged in series (where transfer functions are multiplied).

Figure 3A:
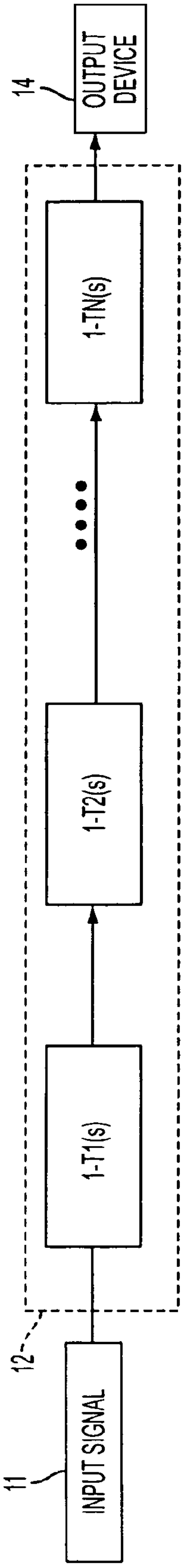
FIG. 3A PRIOR ART
FIG. 3A is a general block diagram of a typical prior art multi-band audio equalizer, similar to FIG. 1, but with multiple bands.

FIG. 3A is a general block diagram of a typical prior art multi-band audio equalizer, similar to FIG. 1, but with multiple eq type bands/sections (each of which may be identical, or with different or overlapping frequency ranges). These are connected in series, which produces the desired effect for these devices. The gain of each band's transfer function T may vary from above 0 to below 0, allowing both boost and cut.

Figure 3B:
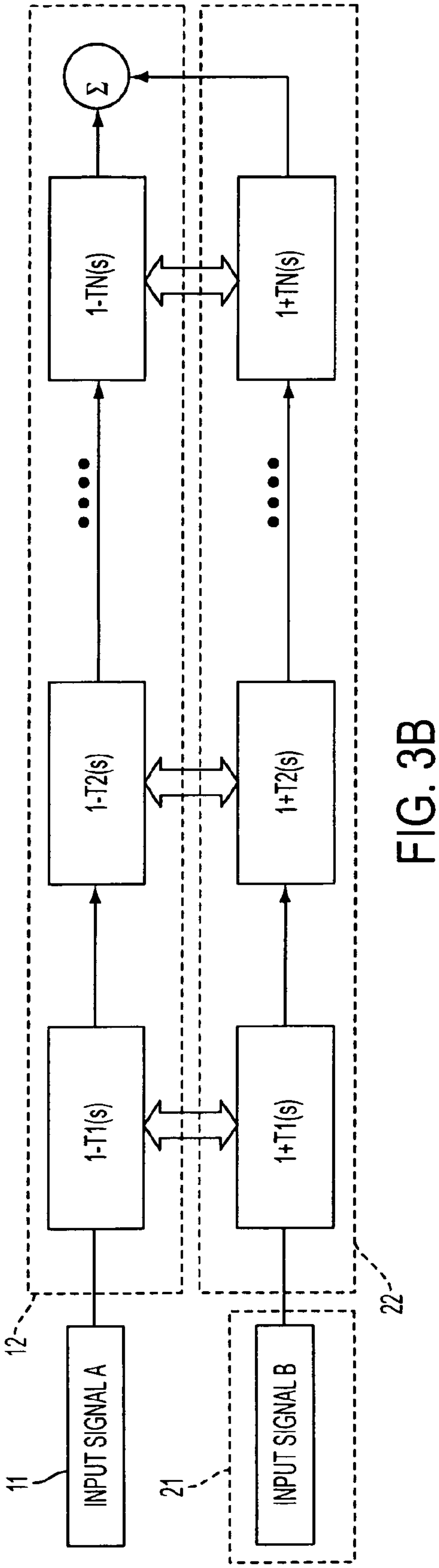
FIG. 3B is a general block diagram of the device of FIG. 3A, adapted for the addition of inverse filter elements, according to an embodiment of the present invention.

FIG. 3B shows this scenario adapted for the addition of inverse filter elements, according to an embodiment of the present invention, where the secondary channel elements are eq type filters. Here also, the gain of each band's transfer function T may vary from −1 to +1, allowing both boost and cut. This arrangment introduces a definable error. Ideal operation maintains the gain relationship as indicated above; if both channels 12 and 22 receive the same input, $11=21=V_{in}$, the mixed output remains $2\cdot V_{in}$ no matter what the EQ settings. With multiple EQ bands, the inputs to the second band pair are altered by the first band pair, and are no longer equivalent. As soon as there are two bands in series for both channels, with the channels then mixed together, the output transfer function, $$In_A\cdot(1-T\mathbf{1}(s))\cdot(1-T\mathbf{2}(s))+In_B\cdot(1+T\mathbf{1}(s))\cdot(1+T\mathbf{2}(s))$$

no longer reduces to $2\cdot V_{in}$ when $In_A=In_B=V_{in}$, but becomes $$(2+2\cdot T\mathbf{1}(s)\cdot T\mathbf{2}(s))\cdot V_{in}.$$

This error increases for each additional band. If all filters T1(*s*) . . . TN(s) are narrow bandpass filters with significantly different pole frequencies, the error can be kept to within ±2 dB across the spectrum. The error created by this series arrangement may be tolerable if independence of the inputs is to be maintained. Maintaining independence is useful in many circumstances, such as when manipulating a stereo pair. The separate set of controls 24 shown in FIG. 2B, allowing individual adjustments to the secondary channel parameters for each band, allow an operator to compensate for this error. Alternatively, the system may be configured as a graphic equalizer with fixed frequency and Q for each band, only varying the gains. A scenario such as this can be arranged to limit the multi-band error to a small tolerance.

Figure 3C:
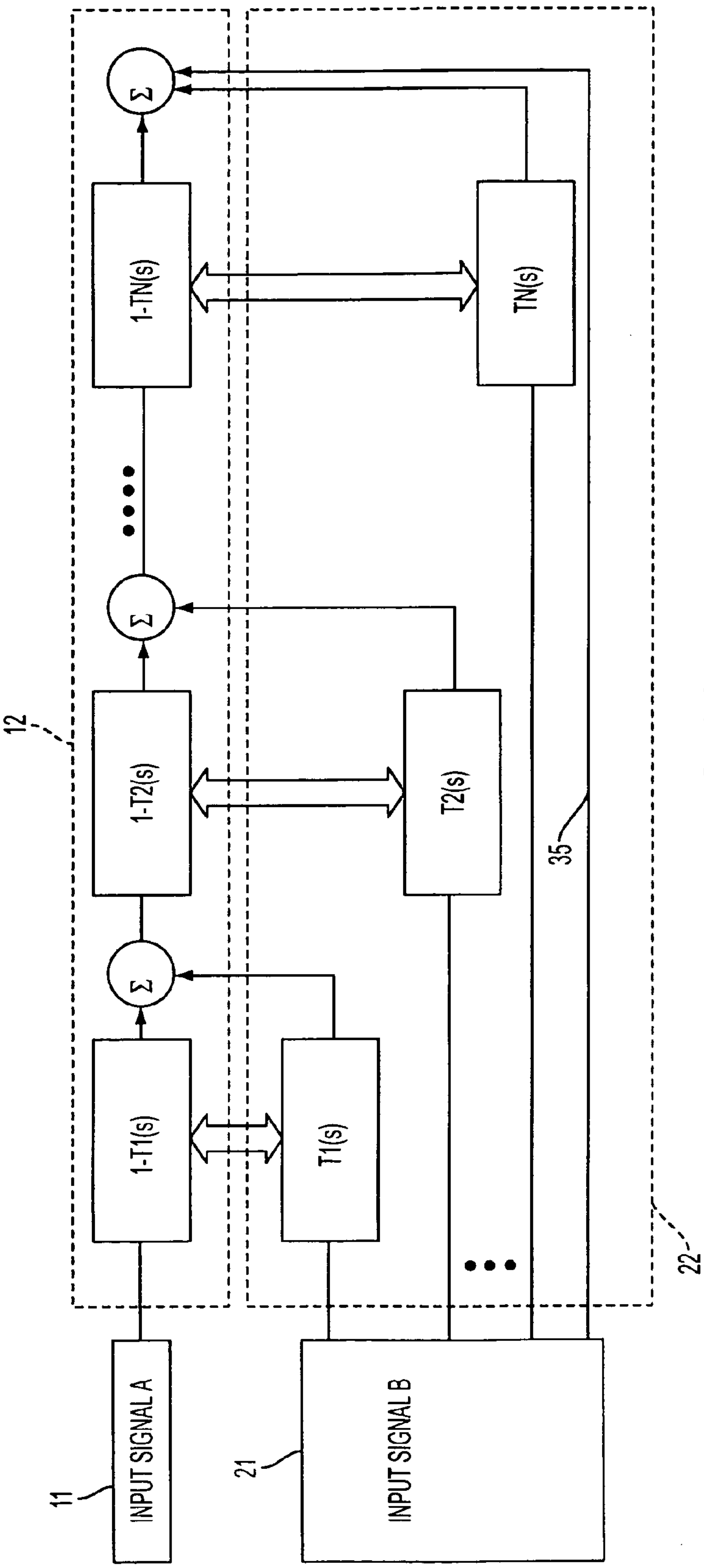
FIG. 3C is a general block diagram of a second multiple band version of an audio equalizer arranged for the addition of inverse filter elements, according to an embodiment of the present invention.

FIG. 3C shows an arrangement which reduces or eliminates this error. As above, the gain of each band's transfer function T may vary from −1 to +1, allowing both boost and cut, but all elements of secondary channel 22 must be of the simple filter type. Also changed here from FIG. 3B are the inputs and outputs of each band of secondary channel 22. Each band's secondary element receives its input directly from secondary input signal 21, and the output of each band's secondary element is supplied to the input of the next band's PRIMARY element. The output transfer function is $$\{[In_A\cdot(1-T\mathbf{1}(s))+In_B\cdot T\mathbf{1}(s)]\cdot[1-T\mathbf{2}(s)]+In_B\cdot T\mathbf{2}(s)\}\ldots\cdot\ldots(1-TN(s))+In_B\cdot TN(s)+In_B$$

With both inputs equal to $V_{in}$, the expression can be factored as:

$$V_{in}\cdot[\{[(1-T\mathbf{1}(s))+T\mathbf{1}(s)]\cdot[1-T\mathbf{2}(s)]+T\mathbf{2}(s)\}\ldots\cdot\ldots(1-TN(s))+TN(s)+1]$$

which reduces to $2V_{in}$. The addition of secondary channel input 21 to the final output, shown as line 35, is required for the simple filter elements of secondary channel 22 to operate with both boost and cut.

Figure 3D:
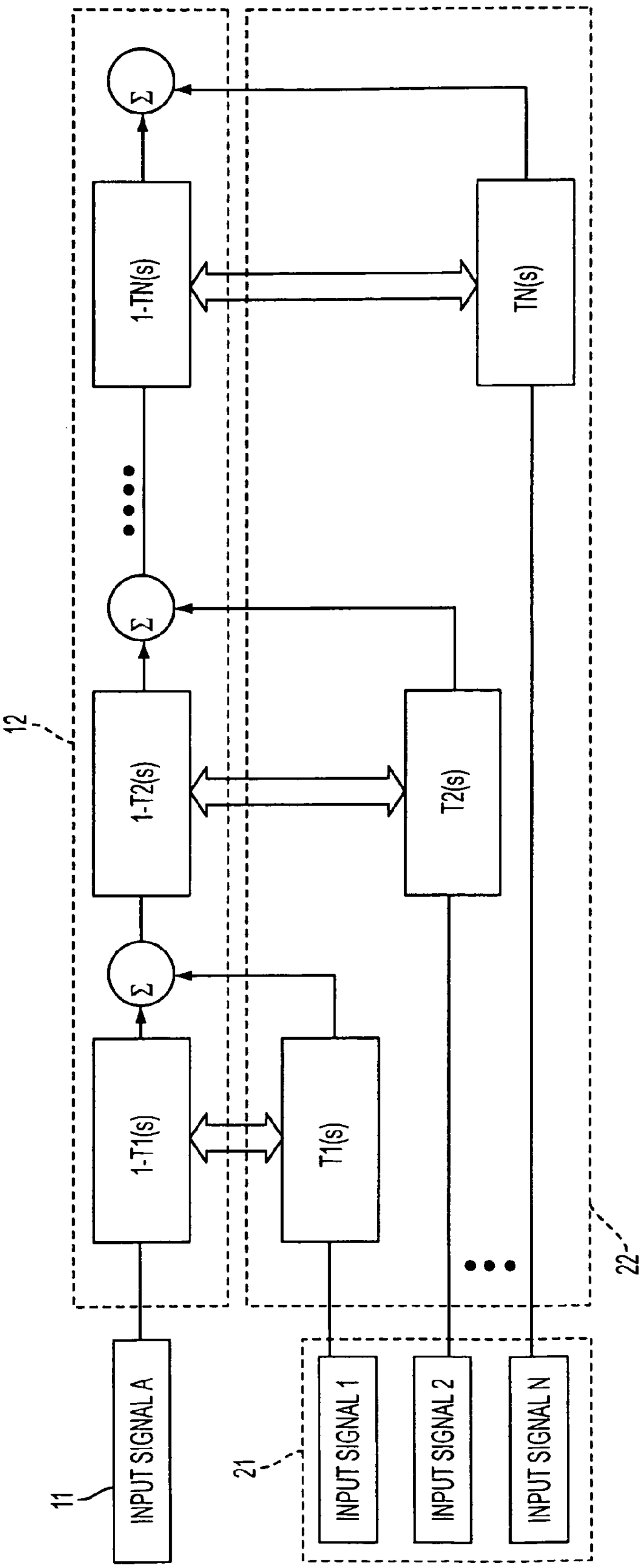
FIG. 3D is a general block diagram of a third multiple band version of an audio equalizer arranged for the addition of inverse filter elements, according to an embodiment of the present invention.

FIG. 3D is a general block diagram of an arrangement which avoids this error for a primary/secondary pair of channels with a multiplicity of bands 12/22 and a multiplicity of secondary inputs 21 (any or all of the secondary inputs 21 may be from a single source). All elements of secondary channel 22 should be of the simple filter type. The gain of each band's transfer function T may vary only from 0 to +1, allowing only cut in the primary channel filters. As in FIG. 3C, the filter functions are here incorporated at each step. There are no errors in maintaining gain relationships when all the inputs of 11 and 21 are equal, other than errors of construction tolerances. By mixing the outputs of each band pair and by using the mix as the input to the next band of the primary EQ, the multiple bands remain functionally independent from each other. As above, a filter is represented by T(s), and an equalizer by (1−T(s)). The final transfer function of the device is as follows:

$$\{[In_A\cdot(1-T\mathbf{1}(s))+In_1\cdot T\mathbf{1}(s)]\cdot[1-T\mathbf{2}(s)]+In_2\cdot T\mathbf{2}(s)\}\ldots\cdot\ldots(1-TN(s))+In_N\cdot TN(s)$$

With all inputs equal to $V_{in}$, the expression can be factored as:

$$V_{in}[\{[(1-T\mathbf{1}(s))+T\mathbf{1}(s)]\cdot[1-T\mathbf{2}(s)]+T\mathbf{2}(s)\}\ldots\cdot\ldots(1-TN(s))+TN(s)]$$

which equals $V_{in}$. The meaning of this equivalency is that there is a direct replacement of frequencies from one channel to another.

Rather than being fed to the succeeding primary channel filter inputs, the outputs of each secondary channel filter section of FIG. 3D may be summed separately to maintain channel independence, although accuracy is compromised. If all filters T1(*s*)~TN(s) are narrow bandpass filters with significantly different pole frequencies, the error can be kept to within ±2 dB across the spectrum. The separate set of controls 24 shown in FIG. 2B, allowing individual adjustments to the secondary channel parameters for each band, allow an operator to compensate for this error.

The embodiments of FIGS. 3B and 3C are most appropriate where 2 useful signals are present, and one wants to affect certain frequency ranges of these two complementarily (boost one and cut the other). The embodiments of FIG.

3D are most appropriate when one wants to cut problematic frequency ranges of an otherwise useful signal, and 'fill them in' (replace them) with useful sections of an otherwise undesireable signal.

Figure 4:
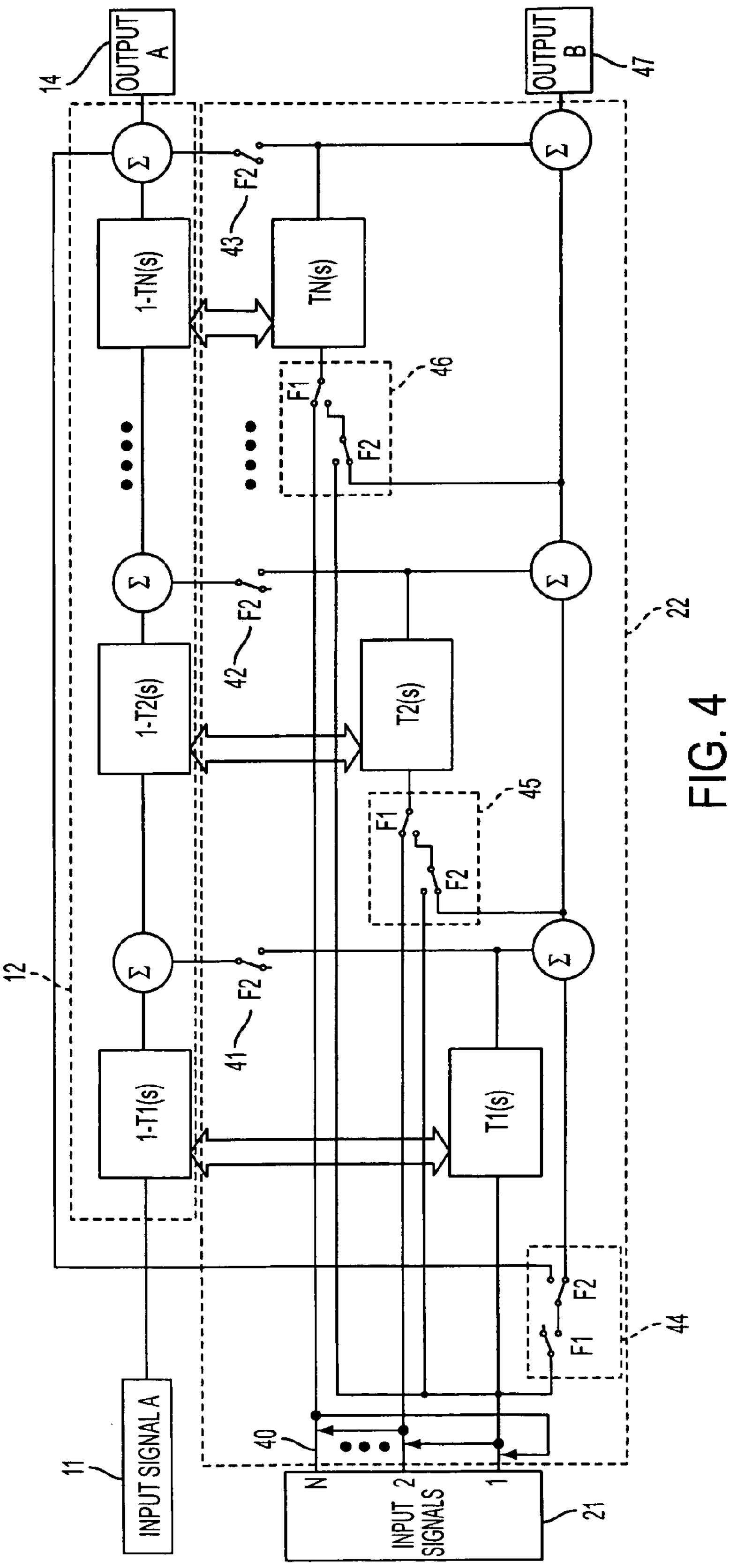
FIG. 4 is a general block diagram of an embodiment with a switching arrangement which allows a user to choose one of the embodiments of FIGS. 3A, 3B, 3C, and 3D from within a single device.

FIG. 4 is a general block diagram of an embodiment with a switching arrangement which allows a user to choose one of the embodiments of FIGS. 3A, 3B, 3C, and 3D from within a single device. Since the switching process is a straightforward implementation of the elements discussed above, a detailed descripton is not necessary here. Switch elements labeled the same (e.g., all switches marked F1) operate as a unit, and are toggled by a single user selection. The switching process must enable certain gain adjustments for proper operation.

The method suggests that exceptional benefits may be derived by constructing special devices for specific situations. One appropriate example arises when recording a drum set, where there are several sound sources in close proximity. It is common to record each element of the drum set (bass drum, snare drum, hi-hat cymbal pair, tom-toms, other cymbals, etc.) with a separate microphone and channel, so that the tone quality and relative volume levels may be adjusted as desired later. The sound of each instrument will be present, to some degree, in all the other instruments' microphones. This unwanted signal is called crosstalk.

A common problem is encountered when some frequencies above 1 kHz from the hi-hat signal appear with great strength in the microphone placed above the snare drum, only a few inches from the hi-hat. The offending frequency spectrum can be equalized out of this signal, but, because those frequencies are an important part of the snare drum's sound, the resulting signal is defficient in the filtered region. This filtered signal from the microphone above the drum no longer has the problematic hi-hat crosstalk, but also has little of the high frequencies of the drum itself, which are very important for this instrument—what remains is a good representation of the drum's lower frequency range.

Placing a microphone underneath the snare drum reduces the crosstalk from the hi-hat significantly, because the drum itself is between the microphone and the offending hi-hat, and so acts as a sound barrier. But the sound underneath is a poor representation of the sound of the drum. Placement underneath misses the major contribution of the top drumhead's sound, caused partly by the sound of the contact by the drumstick which strikes it. Thus, the drum's low frequencies sound uncharacteristic below the drum, and it can be helpful to filter them out, leaving only the higher frequencies. Also, a significant portion of the snare drum signal's high frequency energy comes from the snares. These are usually metal springs which vibrate against the outside of the bottom head, underneath the drum. A microphone underneath the drum receives a disproportionate amount of this high frequency signal, compared to the normal sound of the drum. This filtered signal from a microphone below the drum is missing the problematic hi-hat crosstalk, but also has little of the drum's low frequencies—what remains is a good, but overly strong, representation of the drum's higher frequency range.

A summary of the results above is:

Signal from microphone above the drum, after hi frequencies are filtered out:

1—good low frequency drum signal
2—inadequate high frequency drum signal
3—low hi-hat crosstalk signal.

Signal from microphone below the drum after low frequencies are filtered out:

1—inadequate low frequency drum signal
2—good, but overly strong, high frequency drum signal
3—low hi-hat crosstalk signal.

Combining the results of the two filtered microphone signals results in a good full frequency representation of the snare drum, with a reduction in the crosstalk from the hi-hat. The signal from above the drum contributes only low frequencies, with no high frequency signal from either drum or hi-hat. The overly strong high frequency signal from below the drum requires that we use less of this signal in the combined signal, which advantageously further reduces the unwanted hi-hat crosstalk. Optimums for the difference in signal strength, and the shapes and poles of the filters, have been determined by experiment, and are given in the description which follows.

Figure 5:
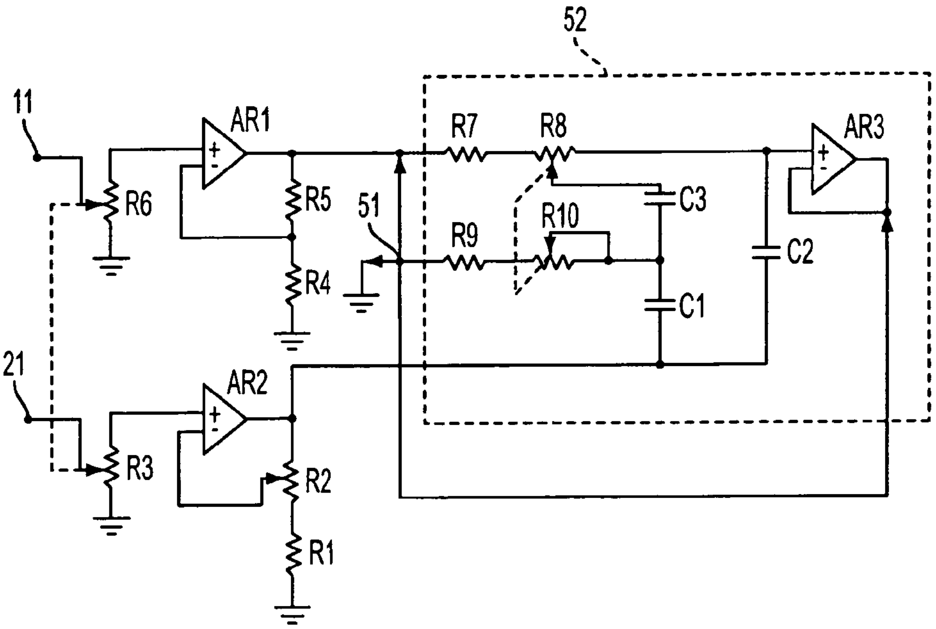
FIG. 5 is a schematic diagram of an embodiment of the present invention designed specifically for use with two microphones, and optimized to reduce the acoustic crosstalk from a hi-hat in a signal from a snare drum.

Referring to FIG. 5, the gain of microphone pre-amp AR2 (used for the microphone below the drum) is set to track about −9 dB lower than the the gain for pre-amp AR1 (used for the microphone above the drum). This assumes the use of microphones with equivalent sensitivity and signal level, each of the 2 microphones being placed about 1 inch from its appropriate drumhead. At this gain ratio, the resulting combined output sounds most similar to the acoustic sound when mixed at a majority of frequency settings determined by the dual potentiometer R8+R10. The user can vary the level of bottom microphone 21's signal independently with variable resistor R2 to account for differences in microphones, snare timbre, placement, and taste. A single gain control, dual potentiometer R3+R6, varies the pre-amp gain applied to both signals 11 (above drum microphone) and 21 (below drum microphone) in tandem. This maintains the set gain ratio, which allows the user to adjust level without worrying about the balance of the microphone signals.

The filter circuit 52 of FIG. 5 acts as a variable-frequency low pass for input signal 11 (from the microphone above the drum) and as a variable-frequency high pass for input signal 21 (from the microphone below the drum). At the highest frequency setting, the pole frequency for the low pass overlaps the pole frequency for the high pass by approximately one octave. Both poles are adjusted simultaneously with the single control (R8+R10). As the pole frequencies are lowered, the overlap of the frequency poles drops to less than a third of an octave. In this example, the high pass responds as a first-order filter in parallel with a second-order filter. Also, in this example, the low pass filter is comprised of two first-order filters in series, with resonance. When the pole frequency is at its highest, the high-pass first-order function dominates, but the low pass is second order with matching poles. When the pole is lowest, the high-pass second-order function dominates, but the low pass is first order. Connection 51 can be to a) signal 11's pre-amp output, b) ground, or c) filter circuit 52's output, each yielding a slightly different frequency response at the crossover frequencies. Scenarios a) and b) differ only in the top mic's resonance response, whereas c) adds resonance to both filter functions. Our experimentation shows that the approximate useful low-pass frequency range is 160 Hz to 8 kHz, and the approximate useful high-pass frequency range is 125 Hz to 4 kHz.

Figure 6:
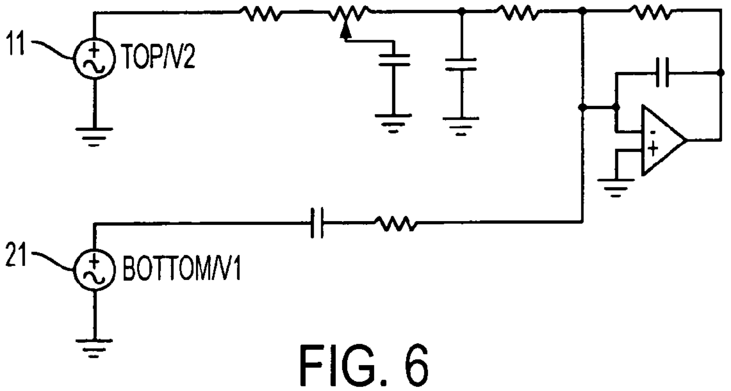
FIG. 6 is a first simplified version of filter portion 52 of the embodiment in FIG. 5.
Figure 7:
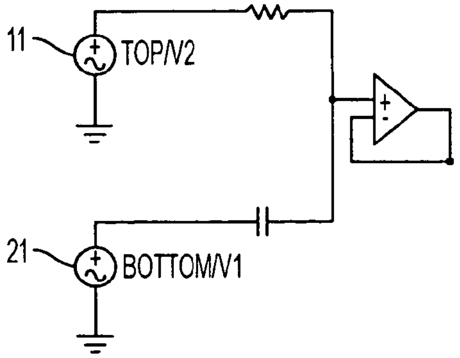
FIG. 7 is a second simplified version of filter portion 52 of the embodiment in FIG. 5.

FIGS. 6 and 7 are simplified filter section versions of the example of FIG. 5, where a cost savings can be attained in circumstances that will allow for it. In FIG. 6, input signal 11's low-pass frequency pole and filter slope vary as in FIG. 5, but the filter pole for the input signal 21 (from the microphone below the drum) is fixed at about 1 kHz. FIG. 7 is an even simpler version, with poles for both the low-pass and high-pass filters fixed at about 1 kHz. They are shown here as first-order filter functions, but other filter orders can be easily constructed.

Figure 8:
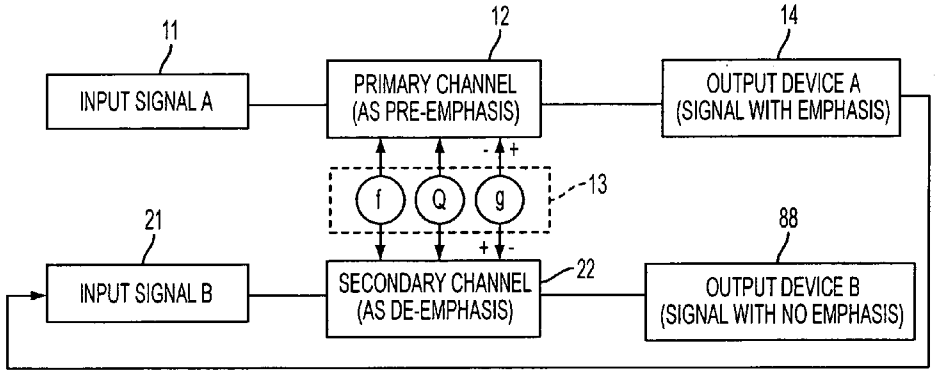
FIG. 8 is FIG. 2A, arranged for use as a frequency emphasis/de-emphasis device.

FIG. 8 shows an embodiment for another use of the present invention, as a variable emphasis/de-emphasis noise-reduction device. Primary Channel 12 adds emphasis by boosting a region, and Secondary Channel 22 de-emphasizes by cutting the same region. In this case, the gain relationships should be maintained not when summed, (i.e., mixed in parallel) but rather when multiplied (i.e., used in series); therefore output device 14 is inserted between 12 and 22—the output of 14 becomes the Input Signal 21. To preserve unity gain from input to output, the total transfer function of 12 must be the reciprocal of the total transfer function of 22. The result is transparent for any linear function of processing implemented in the device/s 14. Since multiplication is associative, a multiplicity of bands can be used in series without any errors described in previous designs. Note that since the reciprocal of infinite cut is infinite boost, infinite cut is not possible.

Another specific application is for use with any acoustical instrument, such as the guitar. The guitar is commonly used with three common transducer types: air pressure microphones, accelerometer (physical vibration induction) pickups, and magnetic induction pickups. The most faithful reproduction is accomplished by the use of a high quality air pressure microphone. For truest fidelity, the microphone is placed at least as far from the instrument as the largest sound producing dimension of the instrument; for a guitar, this distance is between 0.5 and 1.0 meters. These microphones respond to all sound in the acoustic environment, creating problems with isolation and feedback (discussed below).

An accelerometer pickup induces energy from the physical vibrations of a particular part of the guitar's material body, usually the wood near the bridge (the energy from the strings is transmitted through the bridge to the rest of the instrument, so the vibrations are strongest there). The vibrations so induced are somewhat like the air-born sound waves which we normally hear, and the result, if done carefully, is a mediocre but recognizable instrument sound. These pickups do not suffer from isolation and feedback problems nearly as much as air pressure microphones.

A magnetic induction pickup requires the instrument to have metal strings, necessary to create the magnetic field which is then induced. The instrument is not required to (and most commonly does not) produce enough acoustic energy to be heard without the amplification for which it was designed, though it arose out of attempts to amplify pre-existing acoustic instruments. The sound produced only remotely resembles that produced by an instrument's body, but has given rise to what are essentially new instruments, such as the electric guitar, electric bass, and electric violin.

Acoustic guitars provide enough acoustic energy to be heard without assistance, but the amount of energy is small, and limits un-amplified use to a small range of circumstances. In the presence of a large space or other instruments, amplification is generally needed. When enough sound from the amplification system gets into the system source (the microphone or other transducer), a positive feedback loop is often created that drives the speaker amplifier into saturation, producing a loud howl. This is a common occurrence. The feedback generally occurs at specific frequency regions that are emphasized by accidental (random) circumstances of instrument construction, room construction, and placement of the instrument and transducer within the room and with relation to the amplification system. Air pressure devices are more sensitive to this problem than the other, lower fidelity induction devices. After optimizing for these circumstances, the common prior art corrective is to use a device such as an equalizer 12 (FIGS. 1, 3A) to reduce the level of the signal in the problematic frequency bands. This lowers the fidelity of the reduced signal, and a compromise must be reached.

A complimentary-pair equalizer according to an embodiment of the present invention may greatly improve the quality of sound in this circumstance. In one embodiment, a high-fidelity (e.g., air pressure microphone) signal is used as Primary Input Signal 11, and a lower fidelity (e.g., accelerometer 'pickup') signal is used as Secondary Input Signal 21. An appropriate embodiment may be used, such as one of those in the FIGS. 2A, 2B, 3B, 3C, or 3D. In the prior art, frequency bands which include feedback in the acoustic microphone are merely reduced. The present invention not only reduces these bands from the (primary) acoustic to microphone signal, but replaces them with the (secondary) accelerometer signal from the same bands. This may provide a higher fidelity overall signal quality than that from the accelerometer alone, and may also greatly increase the gain-before-feedback level available with only an air pressure microphone.

Although embodiments are specifically illustrated and described herein, it will be appreciated that modifications and variations of the present invention are covered by the above teachings and within the purview of the appended claims without departing from the spirit and intended scope of the invention. For example, though many of the circuits described above are designed for use with analog signals, one skilled in the art, given the teachings above, will appreciate that these circuits may be modified to handle digital signals as well.

What is claimed is:

1. A method of processing signals comprising:

Providing a first signal and a second signal, each of said first and second signals comprising a frequency spectrum including a plurality of frequency bands;

Supplying said first and second signals to first and second signal processors, respectively;

Selecting at least one of said plurality of frequency bands with said first signal processor and selecting at least one of said plurality of frequency bands with said second signal processor, wherein said selections are less than the frequency spectrum of the plurality of frequency bands for said first and second signals;

Adjusting the level of the first and second signals prior to providing said first and second signals to said signal processors; and Adjusting a level for the at least one frequency band selected by said first processor with said first processor, and adjusting a level for the at least one frequency band selected by said second processor with said second processor, such that an increase in level of said selected at least one frequency band in one of said first and second signals results in a decrease in level of said selected at least one frequency band in the other of said first and second signals, and said increase in level and said resultant decrease in level are performed independently of changes to other frequency bands in said first and second signal processors.

2. The method of claim 1 further comprising:

Separately adjusting said selected frequency bands for the first and second signals.

3. The method of claim 1 wherein said selections are the same in both of said first and second signal processors.

4. The method of claim 1 further comprising combining said first and second signals after said adjusting step.

5. A method of processing signals comprising:

Providing a first signal from a first position relative to an instrument and a second signal from a second position relative to said instrument, each of said first and second signals comprising a frequency spectrum including a plurality of frequency bands;

Supplying said first and second signals to at least first and second signal processors, respectively;

Selecting at least one of said plurality of frequency bands with said at least first signal processor and selecting at least one of said plurality of frequency bands with said at least second signal processor, wherein said selections are less than the frequency spectrum of the plurality of frequency bands for said first and second signals, and;

Adjusting a level for the at least one frequency band selected by said first processor with said first processor, and adjusting a level for the at least one frequency band selected by said second processor with said second processor, such that an increase in level of said selected at least one frequency band in one of said first and second signals results in a decrease in level of said selected at least one frequency band in the other of said first and second signals, and said increase in level and said resultant decrease in level are performed independently of changes to other frequency bands in said first and second signal processors.

6. The method of claim 5 further comprising:

Adjusting a gain of said first and second signals prior to supplying said first and second signals to said at least first and second signal processors.

7. The method of claim 5 wherein said instrument is a snare drum and said first location is above said snare drum and said second location is below said snare drum.

8. The method of claim 7 wherein in said adjusting step, a preset ratio of a gain for the second signal is between 11 and 5 dB lower than said gain for said first signal.

9. The method of claim 5 wherein one of said first and second signal processors is a high-pass filter and the other of said first and second signal processors is a low pass-filter.

10. The method of claim 9 where a pole for each of said filters is set at 1 kHz.

11. The method of claim 9 where a pole of the high-pass filter is set at 1 kHz, and a pole of the low-pass filter is variable between a first order low-pass at approximately 160 Hz and a second order low-pass at approximately 8 kHz.

12. The method of claim 9 further comprising:

Adjusting a pole for each of said high-pass and low-pass filters.

13. The method of claim 9 where at high frequency poles said high-pass and low-pass filters overlap approximately one octave and at low frequency poles said high-pass and low-pass filter overlap approximately one-third of an octave.

14. The method of claim 12 where an approximate adjustment range of the high-pass filter frequency pole is between 160 Hz and 8 kHz, in conjunction with an approximate adjustment range of the low-pass filter being between 125 Hz to 4 kHz.

15. The method of claim 5 wherein said selections are the same in both of said at least first and second signal processors.

16. The method of claim 5 further comprising combining said first and second signals after said adjusting step.

17. An apparatus for processing signals comprising:

a first signal source adapted to provide a first signal from a first position relative to an instrument and a second signal source adapted to provide a second signal from a second position relative to said instrument, each of said first and second signals comprising a frequency spectrum including a plurality of frequency bands;

first and second signal processors adapted to receive said first and second signals, respectively;

said first signal processor further adapted to select at least one of said plurality of frequency bands, wherein said selection is less than the frequency spectrum of the plurality of frequency bands for said first signal;

second signal processor further adapted to select at least one of said plurality of frequency bands, wherein said selection is less than the frequency spectrum of the plurality of frequency bands for said second signal; and the first signal processor further adapted to adjust a level for the at least one frequency band selected by said first processor, and said second signal processor further adapted to adjust a level for the at least one frequency band selected by said second processor, such that an increase in level of said selected at least one frequency band in one of said first and second signals results in a decrease in level of said selected at least one frequency band in the other of said first and second signals, and said increase in level and said resultant decrease in level are performed independently of changes to other frequency bands in said first and second signal processors.

18. The apparatus of claim 17 wherein said instrument is a snare drum and said first location is above said snare drum and said second location is below said snare drum.

19. The apparatus of claim 17 wherein said first signal source includes an acoustic pressure microphone and said second signal source includes an accelerometer pickup.

20. The apparatus of claim 17 wherein said first signal source includes an acoustic pressure microphone and said second signal source includes an electromagnetic pickup.

21. The apparatus of claim 17 wherein said at least one of said plurality of frequency bands selected by said first and second processors are the same.

22. The apparatus of claim 17 further comprising a mixer to combine said first and second signals after said adjusting step.

23. A method of processing signals comprising:

Providing a first signal and a second signal, each of said first and second signals comprising a frequency spectrum including a plurality of frequency bands;

Supplying said first and second signals to first and second signal processors, respectively;

Selecting at least one of said plurality of frequency bands with said first signal processor and selecting at least one of said plurality of frequency bands with said second signal processor, wherein said selections are less than the frequency spectrum of the plurality of frequency bands for said first and second signals;

Adjusting a level for the at least one frequency band selected by said first processor with said first processor, and adjusting a level for the at least one frequency band selected by said second processor with said second processor, such that an increase in level of said selected at least one frequency band in one of said first and second signals results in a decrease in level of said selected at least one frequency band in the other of said first and second signals, and said increase in level and said resultant decrease in level are performed independently of changes to other frequency bands in said first and second signal processors, wherein a magnitude of said increase in level is equal to a magnitude of said decrease in level, and combining said first and second signals after said adjusting step.

24. An apparatus for processing signals comprising:

a first input to receive a first signal from a first signal source and a second input to receive a second signal from a second signal source, each of said first and second signals comprising a frequency spectrum including a plurality of frequency bands;

first and second signal processors adapted to receive said first and second signals, respectively;

said first signal processor further adapted to select at least one of said plurality of frequency bands, wherein said selection is less than the frequency spectrum of the plurality of frequency bands for said first signal;

said second signal processor further adapted to select at least one of said plurality of frequency bands, wherein said selection is less than the frequency spectrum of the plurality of frequency bands for said second signal;

the first signal processor further adapted to adjust a level for the at least one frequency band selected by said first processor, and said second signal processor further adapted to adjust a level for the at least one frequency band selected by said second processor, such that an increase in level of said selected at least one frequency band in one of said first and second signals results in a decrease in level of said selected at least one frequency band in the other of said first and second signals, and said increase in level and said resultant decrease in level are performed independently of changes to other frequency bands in said first and second signal processors, wherein a magnitude of said increase in level is equal to a magnitude of said decrease in level, and;

a mixer to combine said first and second signals from said first and second signal processors.

25. An apparatus for processing signals comprising:

a first input to receive a first signal from a first signal source and a second input to receive a second signal from a second signal source, each of said first and second signals comprising a frequency spectrum including a plurality of frequency bands;

first and second signal processors adapted to receive said first and second signals, respectively;

said first signal processor further adapted to select at least one of said plurality of frequency bands, wherein said selection is less than the frequency spectrum of the plurality of frequency bands for said first signal;

said second signal processor further adapted to select at least one of said plurality of frequency bands, wherein said selection is less than the frequency spectrum of the plurality of frequency bands for said second signal;

the first signal processor further adapted to adjust a level for the at least one frequency band selected by said first processor, and said second signal processor further adapted to adjust a level for the at least one frequency band selected by said second processor, such that an increase in level of said selected at least one frequency band in one of said first and second signals results in a decrease in level of said selected at least one frequency band in the other of said first and second signals, and said increase in level and said resultant decrease in level are performed independently of changes to other frequency bands in said first and second signal processors, wherein a magnitude of said increase in level is equal to a magnitude of said decrease in level, and;

wherein means are provided for separately adjusting the level of the first and second signals prior to providing said first and second signals to said signal processors.

* * * * *